(12) United States Patent
Wolcott et al.

(10) Patent No.: US 10,456,014 B2
(45) Date of Patent: Oct. 29, 2019

(54) WATER BOTTLE CAP ASSEMBLIES FOR AN ENDOSCOPIC DEVICE

(71) Applicant: UNITED STATES ENDOSCOPY GROUP, INC., Mentor, OH (US)

(72) Inventors: Kenneth E. Wolcott, Centerport, NY (US); Jeffrey B. Cushner, Woodmere, NY (US); Ethan J. Mandelup, Long Island City, NY (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 0 days.

(21) Appl. No.: 14/387,309

(22) PCT Filed: Mar. 15, 2013

(86) PCT No.: PCT/US2013/032005
§ 371 (c)(1),
(2) Date: Sep. 23, 2014

(87) PCT Pub. No.: WO2013/148311
PCT Pub. Date: Oct. 3, 2013

(65) Prior Publication Data
US 2015/0297063 A1    Oct. 22, 2015

Related U.S. Application Data

(60) Provisional application No. 61/618,054, filed on Mar. 30, 2012.

(51) Int. Cl.
*A61B 1/00* (2006.01)
*A61B 1/015* (2006.01)

(52) U.S. Cl.
CPC ...... *A61B 1/00128* (2013.01); *A61B 1/00119* (2013.01); *A61B 1/00137* (2013.01); *A61B 1/015* (2013.01)

(58) Field of Classification Search
CPC . A61B 1/00128; A61B 1/015; A61B 1/00137; A61B 1/00119; A61B 1/00068; A61B 1/126
(Continued)

(56) References Cited

U.S. PATENT DOCUMENTS 1,034,170 A    7/1912   Vanier
2,186,908 A    1/1940   Page et al.
(Continued)

FOREIGN PATENT DOCUMENTS

DE    33 24 730 A1    1/1984
EP    0075153 A2      3/1983
(Continued)

OTHER PUBLICATIONS

Office Action for Canadian Application No. 2,772,341 dated Nov. 3, 2014.
(Continued)

*Primary Examiner* — Timothy J Neal
(74) *Attorney, Agent, or Firm* — Calfee, Halter & Griswold LLP

(57) ABSTRACT

Embodiments of the present invention provide water bottle cap assemblies suitable for attachment to an endoscopic device and a water source. For example, the water bottle cap assembly includes a cap comprising a plurality of ports and an engageable member configured to sealingly engage with a water source. The assembly also includes a plurality of tubular members, each tubular member coupled to a respective port so as to be in fluid communication therewith. In addition, the assembly includes an adaptor coupled to an end of one of the tubular members and configured to couple to an endoscopic device, wherein at least one of the tubular members is configured to convey at least one fluid between the water source and the endoscopic device.

15 Claims, 7 Drawing Sheets

US 10,456,014 B2

Page 2

(58) Field of Classification Search
USPC .................................. 600/104, 153–159
See application file for complete search history.

(56) References Cited

U.S. PATENT DOCUMENTS

| | | | |
|---|---|---|---|
| D189,383 S | 11/1960 | Macomber | |
| 3,135,412 A | 6/1964 | Cornelius | |
| 3,222,135 A | 12/1965 | Ashmead | |
| 3,390,897 A | 7/1968 | Buell | |
| D227,558 S | 7/1973 | Matthews, Jr. | |
| 4,108,172 A | 8/1978 | Moore, Jr. | |
| 4,258,721 A | 3/1981 | Parent et al. | |
| 4,261,343 A | 4/1981 | Ouchi et al. | |
| 4,261,345 A | 4/1981 | Yamaguchi | |
| 4,262,671 A | 4/1981 | Kersten | |
| 4,311,134 A | 1/1982 | Mitsui et al. | |
| 4,319,690 A | 3/1982 | Birrell et al. | |
| 4,325,362 A | 4/1982 | Ouchi et al. | |
| 4,350,647 A | 9/1982 | De la Cruz | |
| D267,743 S | 1/1983 | Cummingham et al. | |
| D271,618 S | 11/1983 | Nishigaki | |
| 4,464,316 A | 8/1984 | Michaels | |
| 4,474,574 A | 10/1984 | Wolfe et al. | |
| 4,489,712 A | 12/1984 | Ohshima | |
| 4,494,252 A | 1/1985 | Chaoui | |
| 4,519,385 A | 5/1985 | Atkinson et al. | |
| D280,206 S | 8/1985 | Ishii | |
| 4,538,593 A | 9/1985 | Ishii | |
| 4,539,586 A | 9/1985 | Danna et al. | |
| 4,548,197 A | 10/1985 | Kinoshita | |
| 4,550,716 A | 11/1985 | Kinoshita | |
| 4,552,130 A | 11/1985 | Kinoshita | |
| 4,637,378 A | 1/1987 | Sasa | |
| 4,667,655 A | 5/1987 | Ogiu et al. | |
| 4,691,701 A | 9/1987 | Williams | |
| 4,701,159 A | 10/1987 | Brown et al. | |
| 4,708,126 A | 11/1987 | Toda et al. | |
| 4,748,970 A | 6/1988 | Nakajima | |
| 4,760,838 A | 8/1988 | Fukuda | |
| D299,538 S | 1/1989 | Balding et al. | |
| 4,800,869 A | 1/1989 | Nakajima | |
| 4,844,052 A | 7/1989 | Iwakoshi et al. | |
| 4,857,062 A | 8/1989 | Russell | |
| 4,901,142 A | 2/1990 | Ikuno et al. | |
| 4,905,852 A | 3/1990 | Zumbuhl | |
| 4,968,309 A | 11/1990 | Andersson | |
| 4,997,429 A | 3/1991 | Dickerhoff et al. | |
| 5,027,791 A | 7/1991 | Takahashi | |
| 5,054,481 A | 10/1991 | Shin | |
| 5,083,549 A | 1/1992 | Cho et al. | |
| 5,125,915 A | 6/1992 | Berry et al. | |
| 5,133,336 A | 7/1992 | Savitt et al. | |
| 5,163,576 A | 11/1992 | Galer | |
| 5,176,629 A | 1/1993 | Kullas et al. | |
| 5,192,439 A | 3/1993 | Roth et al. | |
| 5,250,038 A | 10/1993 | Melker | |
| 5,254,083 A | 10/1993 | Gentelia | |
| 5,297,537 A | 3/1994 | Savitt et al. | |
| 5,309,906 A | 5/1994 | LaBombard | |
| 5,333,603 A | 8/1994 | Schuman | |
| 5,343,855 A | 9/1994 | Iida et al. | |
| 5,381,924 A | 1/1995 | Kiefel | |
| 5,402,770 A | 4/1995 | Iida et al. | |
| 5,406,808 A | 4/1995 | Babb | |
| 5,437,654 A | 8/1995 | McVay | |
| 5,505,707 A | 4/1996 | Manzie et al. | |
| 5,607,391 A | 3/1997 | Klinger et al. | |
| 5,630,795 A | 5/1997 | Kuramoto et al. | |
| 5,634,880 A | 6/1997 | Feldman et al. | |
| 5,697,888 A | 12/1997 | Kobayashi et al. | |
| D392,046 S | 3/1998 | Niedospial, Jr. | |
| 5,755,360 A | 5/1998 | Elliott | |
| 5,782,383 A * | 7/1998 | Robinson | A61J 1/1406 215/250 |
| 5,810,718 A | 9/1998 | Akiba et al. | |
| 5,810,770 A | 9/1998 | Chin | |
| 5,830,128 A | 11/1998 | Tanaka | |
| 5,871,111 A | 2/1999 | Pfefferkorn et al. | |
| 5,902,264 A | 5/1999 | Toso et al. | |
| 5,902,413 A | 5/1999 | Puszko et al. | |
| 6,030,632 A * | 2/2000 | Sawan | A01N 25/24 424/405 |
| 6,189,870 B1 | 2/2001 | Withall | |
| 6,210,322 B1 | 4/2001 | Byrne | |
| 6,220,482 B1 | 4/2001 | Simmel et al. | |
| 6,391,000 B1 | 5/2002 | Belikan et al. | |
| 6,481,589 B2 | 11/2002 | Blomdahl et al. | |
| 6,485,412 B1 * | 11/2002 | Byrne | A61B 1/015 600/158 |
| 6,485,684 B1 | 11/2002 | Mapson et al. | |
| 6,558,317 B2 | 5/2003 | Takahashi et al. | |
| 6,575,160 B1 | 6/2003 | Volgyesi | |
| 6,575,946 B2 | 6/2003 | Sealfon | |
| 6,702,738 B2 | 3/2004 | Ito | |
| 6,764,442 B2 | 7/2004 | Ota et al. | |
| 6,786,865 B2 | 9/2004 | Dhindsa | |
| 6,837,400 B2 | 1/2005 | Leoncavallo et al. | |
| 6,840,902 B2 | 1/2005 | Sano et al. | |
| 6,855,109 B2 | 2/2005 | Obata et al. | |
| 6,860,516 B2 | 3/2005 | Ouchi et al. | |
| 6,881,188 B2 | 4/2005 | Furuya et al. | |
| 6,984,204 B2 | 1/2006 | Akiba | |
| 7,066,177 B2 | 6/2006 | Pittaway et al. | |
| 7,297,121 B2 | 11/2007 | Turturro | |
| 7,347,355 B2 | 3/2008 | Sato et al. | |
| 7,399,273 B2 | 7/2008 | Moriyama et al. | |
| 7,568,735 B2 | 8/2009 | Akiba | |
| 7,578,294 B2 | 8/2009 | Pierro et al. | |
| 7,582,056 B2 | 9/2009 | Noguchi et al. | |
| 7,597,662 B2 | 10/2009 | Litscher et al. | |
| D612,496 S | 3/2010 | Bennison | |
| 7,678,044 B2 | 3/2010 | Fujikura | |
| 7,766,898 B2 | 8/2010 | Mottola et al. | |
| 7,806,850 B2 | 10/2010 | Williams, Jr. et al. | |
| 7,824,329 B2 | 11/2010 | Aizenfeld et al. | |
| 7,837,769 B2 | 11/2010 | Lahr | |
| 7,892,223 B2 | 2/2011 | Geiselhart | |
| 7,901,350 B2 | 3/2011 | Yamazaki | |
| 7,914,519 B2 | 3/2011 | Moran et al. | |
| D639,940 S | 6/2011 | Cushner et al. | |
| 7,963,914 B2 | 6/2011 | Uchimura et al. | |
| D652,923 S | 1/2012 | Kennedy et al. | |
| 8,152,716 B2 | 4/2012 | Aizenfeld et al. | |
| 8,343,041 B2 | 1/2013 | Byers et al. | |
| 8,454,498 B2 | 6/2013 | Cushner et al. | |
| 9,049,984 B2 | 6/2015 | Cushner et al. | |
| 9,144,373 B2 | 9/2015 | Kaye et al. | |
| 2001/0044594 A1 | 11/2001 | Martin et al. | |
| 2002/0092858 A1 | 7/2002 | Bowman | |
| 2003/0032860 A1 | 2/2003 | Avni et al. | |
| 2003/0032862 A1 | 2/2003 | Ota et al. | |
| 2003/0045779 A1 | 3/2003 | Ito | |
| 2003/0073971 A1 | 4/2003 | Saker | |
| 2003/0189023 A1 | 10/2003 | Gonzalez | |
| 2004/0153047 A1 | 8/2004 | Blank et al. | |
| 2004/0199052 A1 | 10/2004 | Banik et al. | |
| 2004/0260151 A1 | 12/2004 | Akiba | |
| 2005/0263480 A1 | 12/2005 | Smolko et al. | |
| 2006/0052663 A1 | 3/2006 | Koitabashi | |
| 2006/0052665 A1 | 3/2006 | Aizenfeld et al. | |
| 2006/0068360 A1 | 3/2006 | Boulais | |
| 2006/0106285 A1 | 5/2006 | Boulais et al. | |
| 2006/0135851 A1 | 6/2006 | Yamazaki | |
| 2006/0178648 A1 | 8/2006 | Barron et al. | |
| 2006/0229498 A1 | 10/2006 | Kohno | |
| 2006/0241348 A1 | 10/2006 | Kohno | |
| 2006/0266423 A1 | 11/2006 | Akiba et al. | |
| 2006/0276689 A1 | 12/2006 | Litscher et al. | |
| 2006/0293562 A1 | 12/2006 | Uchimura et al. | |
| 2007/0043261 A1 | 2/2007 | Watanabe et al. | |
| 2007/0043262 A1 * | 2/2007 | Levy | A61B 1/015 600/156 |
| 2007/0066866 A1 | 3/2007 | Noguchi et al. | |
| 2007/0145738 A1 | 6/2007 | Akiba | |

(56) References Cited

U.S. PATENT DOCUMENTS

| | | |
|---|---|---|
| 2007/0129705 A1 | 7/2007 | Trombley, III et al. |
| 2007/0225566 A1 | 9/2007 | Kawanishi |
| 2007/0238929 A1 | 10/2007 | Aizenfeld et al. |
| 2007/0244363 A1 | 10/2007 | Sano et al. |
| 2008/0072970 A1 | 3/2008 | Gasser et al. |
| 2008/0132763 A1 | 6/2008 | Isaacson |
| 2008/0154095 A1 | 6/2008 | Stubkjaer et al. |
| 2008/0214895 A1 | 9/2008 | Campos |
| 2008/0228258 A1 | 9/2008 | Gerdts |
| 2008/0269560 A1 | 10/2008 | Ito et al. |
| 2008/0294123 A1 | 11/2008 | Lunn |
| 2009/0032533 A1 | 2/2009 | Kessell et al. |
| 2009/0101562 A1* | 4/2009 | Newton ............... A61M 3/02 210/232 |
| 2009/0143719 A1 | 6/2009 | Loori et al. |
| 2009/0188919 A1 | 7/2009 | Takanohashi |
| 2009/0209822 A1 | 8/2009 | Ikeda |
| 2009/0260629 A1 | 10/2009 | Yee et al. |
| 2009/0264705 A1* | 10/2009 | Cushner ............... A61B 1/12 600/158 |
| 2009/0266357 A1 | 10/2009 | Varis et al. |
| 2009/0298129 A1 | 12/2009 | Spence et al. |
| 2010/0022834 A1* | 1/2010 | Noda ................. A61B 1/015 600/118 |
| 2010/0056867 A1 | 3/2010 | Labombard |
| 2010/0237070 A1 | 9/2010 | Coonce et al. |
| 2010/0292644 A1 | 11/2010 | Haack |
| 2011/0174822 A1 | 7/2011 | Gasser et al. |
| 2011/0263939 A1* | 10/2011 | Kaye ............... A61B 1/00128 600/158 |
| 2011/0275945 A1 | 11/2011 | Karla et al. |
| 2012/0091092 A1 | 4/2012 | Adams |
| 2012/0209062 A1 | 8/2012 | Qiao |
| 2012/0277536 A1 | 11/2012 | Kaye |
| 2013/0245377 A1 | 9/2013 | Cushner et al. |
| 2014/0316204 A1 | 10/2014 | Ofir et al. |
| 2014/0316205 A1 | 10/2014 | Bendele et al. |
| 2015/0080661 A1 | 3/2015 | Kaye et al. |
| 2015/0297063 A1 | 10/2015 | Wolcott et al. |

FOREIGN PATENT DOCUMENTS

| | | | |
|---|---|---|---|
| EP | 0082950 | A2 | 7/1983 |
| EP | 0361086 | A1 | 4/1990 |
| EP | 0437229 | A1 | 7/1991 |
| EP | 2 428 157 | A1 | 3/2012 |
| JP | 62-125501 | U | 8/1987 |
| JP | 1099558 | A | 4/1989 |
| JP | H01280437 | A | 11/1989 |
| JP | 5168587 | A | 7/1993 |
| JP | 5220103 | A | 8/1993 |
| JP | 5337074 | A | 12/1993 |
| JP | 7-9301 | U | 2/1995 |
| JP | 8106052 | A | 4/1996 |
| JP | 08112251 | A | 5/1996 |
| JP | 9164113 | A | 6/1997 |
| JP | 10099265 | A | 4/1998 |
| JP | 10-276963 | A | 10/1998 |
| JP | 2001299685 | A | 10/2001 |
| JP | 2002 177205 | A | 6/2002 |
| JP | 2003-024266 | A | 1/2003 |
| JP | 2003-070731 | A | 3/2003 |
| JP | 2003111721 | A | 4/2003 |
| JP | 2003-339619 | A | 12/2003 |
| JP | 2004-147833 | A | 5/2004 |
| JP | 2004-242877 | A | 9/2004 |
| JP | 2004-305758 | A | 11/2004 |
| JP | 2005-021710 | A | 1/2005 |
| JP | 2005-245668 | A | 9/2005 |
| JP | 2005-304780 | A | 11/2005 |
| JP | 2006-042874 | A | 2/2006 |
| JP | 2006-110215 | A | 4/2006 |
| JP | 2006-116000 | A | 5/2006 |
| JP | 2006-167064 | A | 6/2006 |
| JP | 2006-280536 | A | 10/2006 |
| JP | 2007-089623 | A | 4/2007 |
| JP | 2007-252834 | A | 10/2007 |
| JP | 2007-313047 | A | 12/2007 |
| JP | 2008-029742 | A | 2/2008 |
| JP | 2010-057728 | A | 3/2010 |
| WO | WO 93/14688 | A1 | 8/1993 |
| WO | 2004023987 | | 3/2004 |
| WO | WO 2006/109351 | A1 | 10/2006 |
| WO | WO-2008/122969 | A1 | 10/2008 |
| WO | WO 2009/129302 | A1 | 10/2009 |

OTHER PUBLICATIONS e-Scope (endoscope sales/services), e-Scope, LLC Brochure, dated Jan. 16, 2008, 2 pages.
Periphery Accessories Programme, PENTAX Brochure, (undated), 20 pages.
Endoscope Channel Guide, Evis™ 40/140/240 & Exera™ 160-Series GI Endoscopes, Olympus America, Inc. (2003), 1 page.
International Preliminary Report on Patentabiity for Application No. PCT/US2010/046805 dated Mar. 15, 2012.
International Search Report and Written Opinion for Application No. PCT/US2010/046805 dated Dec. 7, 2010.
International Search Report and Written Opinion for Application No. PCT/US2010/048578 dated Jan. 28, 2011.
International Search Report and Written Opinion for Application No. PCT/US2009/040655 dated Jun. 29, 2009.
International Preliminary Report on Patentability for Application No. PCT/US2009/040655 dated Oct. 19, 2010.
International Search Report for Application No. PCT/US2014/025948 dated Jul. 29, 2014.
International Search Report and Written Opinion for Application No. PCT/US2013/032005 dated Jun. 18, 2013.
Office Action for Chinese Application No. 201080046225.0 dated May 4, 2014.
Office Action for Chinese Application No. 200980113305.0 dated Nov. 16, 2011.
Notice of Decision of Granting Patent for Application No. 200980113305.0 dated Apr. 9, 2012.
Communication Pursuant to Article 94(3) EPC for Application No. 10 749 572.3; dated Nov. 29, 2013.
Communication for European Patent Application No. 09 731 691.3, dated Dec. 5, 2011, 4 pages.
Office Action for European Application No. 09 731 691.3 dated Oct. 28, 2014.
Office Action for Japanese Application No. 2012-526984; dated May 31, 2013.
Office Action for Japanese Patent Application No. 2011-505165 dated Sep. 21, 2012.
Office Action for U.S. Appl. No. 29/335,431, dated Dec. 7, 2010.
Notice of Allowance for Design U.S. Appl. No. 29/335,421 dated Feb. 10, 2011.
Office Action for U.S. Appl. No. 12/424,211 dated Apr. 23, 2012.
Office Action for U.S. Appl. No. 12/424,211 dated Oct. 5, 2012.
Office Action for U.S. Appl. No. 12/424,211 dated Dec. 4, 2013.
Notice of Allowance for U.S. Appl. No. 12/424,211 dated Mar. 28, 2014.
U.S. Appl. No. 12/869,254, filed Aug. 26, 2010; In re: Cushner et al.; entitled *In-Line Gas Adaptor for Endoscopic Apparatus.*
Office Action for U.S. Appl. No. 12/869,265 dated Aug. 16, 2012.
Notice of Allowance for U.S. Appl. No. 12/869,265 dated Feb. 4, 2013.
Office Action for U.S. Appl. No. 12/881,683 dated Aug. 22, 2012.
Notice of Allowance for U.S. Appl. No. 12/881,683 dated Jul. 2, 2013.
Office Action for U.S. Appl. No. 13/873,598 dated Jul. 30, 2015.
Office Action for U.S. Appl. No. 13/874,568 dated Jul. 30, 2015.
Office Action for U.S. Appl. No. 13/873,598 dated Mar. 26, 2015.
Office Action for U.S. Appl. No. 13/874,568 dated Mar. 26, 2015.
Notice of Allowance for U.S. Appl. No. 14/301,747 dated Mar. 31, 2015.
Office Action for U.S. Appl. No. 13/873,598 dated Nov. 16, 2015.

(56) References Cited

OTHER PUBLICATIONS

Notice of Allowance from U.S. Appl. No. 12/881,683 dated Feb. 7, 2013.
Office Action from U.S. Appl. No. 13/464,263 dated Mar. 11, 2014.
Office Action from U.S. Appl. No. 13/093,989 dated Nov. 10, 2014.
Notice of Allowance from U.S. Appl. No. 13/093,989 dated May 27, 2015.
Office Action from U.S. Appl. No. 14/456,783 dated Mar. 19, 2015.
Response to Office action from U.S. Appl. No. 14/456,783 dated Aug. 19, 2015.
Office Action from U.S. Appl. No. 14/456,783 dated Sep. 10, 2015.
Response to Office Action from U.S. Appl. No. 14/456,783 dated Jan. 11, 2016.
Office Action from U.S. Appl. No. 14/456,783 dated Mar. 10, 2016.
Restriction Requirement from U.S. Appl. No. 14/707,129 dated Sep. 28, 2015.
Response to Restriction Requirement from U.S. Appl. No. 14/707,129 dated Jan. 28, 2016.
Office Action from U.S. Appl. No. 14/707,129 dated Feb. 29, 2016.
Response to Office Action from U.S. Appl. No. 14/707,129 dated Jun. 29, 2016.
Weng et al., "Fundamentals and Material Development for Thermoplastic Elastomer (TPE) Overmolding", in Journal of Injection Molding Technology, vol. 4, No. 1, Mar. 2000.
Office Action from U.S. Appl. No. 14/456,783 dated Jan. 13, 2017.
Response to Office Action from U.S. Appl. No. 14/456,783 dated Sep. 8, 2016.
Office Action from U.S. Appl. No. 14/456,783 dated Sep. 29, 2016.
Office Action from U.S. Appl. No. 14/707,129 dated Sep. 6, 2016.
Amendment from U.S. Appl. No. 14/707,129 dated Dec. 6, 2016.
Response to Office Action from U.S. Appl. No. 14/456,783 dated Dec. 29, 2016.
Office Action from European Application No. 09731691.3 dated Oct. 7, 2016.
Response to Office Action from U.S. Appl. No. 14/456,783 dated May 11, 2017.
Notice of Non-Compliant Amendment from U.S. Appl. No. 14/456,783 dated May 18, 2017.
Response to Notice of Non-Compliant Amendment from U.S. Appl. No. 14/456,783 dated May 18, 2017.
Office Action from U.S. Appl. No. 14/456,783 dated Jun. 7, 2017.
Office Action from U.S. Appl. No. 14/707,129 dated Apr. 21, 2017.
Response to Office Action from U.S. Appl. No. 14/456,783 dated Sep. 7, 2017.
Office Action from U.S. Appl. No. 14/456,783 dated Sep. 20, 2017.
Response to Office Action from U.S. Appl. No. 14/707,129 dated Sep. 29, 2017.
Notice of Allowance from U.S. Appl. No. 14/707,129 dated Oct. 20, 2017.
International Search Report and Written Opinion from Application No. PCT/US2017/025655 dated Sep. 12, 2017.
Amendment from U.S. Appl. No. 14/707,129 dated Jul. 21, 2017.
Office Action from U.S. Appl. No. 14/707,129 dated Aug. 9, 2017.
Response to Office Action from U.S. Appl. No. 14/456,783 dated Jan. 22, 2018.
Office Action from U.S. Appl. No. 14/456,783 dated Mar. 29, 2018.
Response to Office Action from U.S. Appl. No. 14/456,783 dated Jun. 29, 2018.
Notice of Non-Compliant Amendment from U.S. Appl. No. 14/456,783 dated Sep. 10, 2018.
Response to Notice of Non-Compliant Amendment from U.S. Appl. No. 14/456,783 dated Oct. 10, 2018.
Office Action from U.S. Appl. No. 14/456,783 dated Nov. 5, 2018.
Response to Office Action from U.S. Appl. No. 14/456,783 dated Feb. 5, 2019.
Office Action from U.S. Appl. No. 14/456,783 dated Mar. 1, 2019.
Communication Pursuant to Article 94(3) EPC from European Application No. 13714413.5 dated Jul. 30, 2018.
Office Action from U.S. Appl. No. 14/456,783 dated Jun. 14, 2019.
Communication Pursuant to Article 94(3) EPC from European Application No. 13714413.5 dated Jul. 3, 2019.

\* cited by examiner

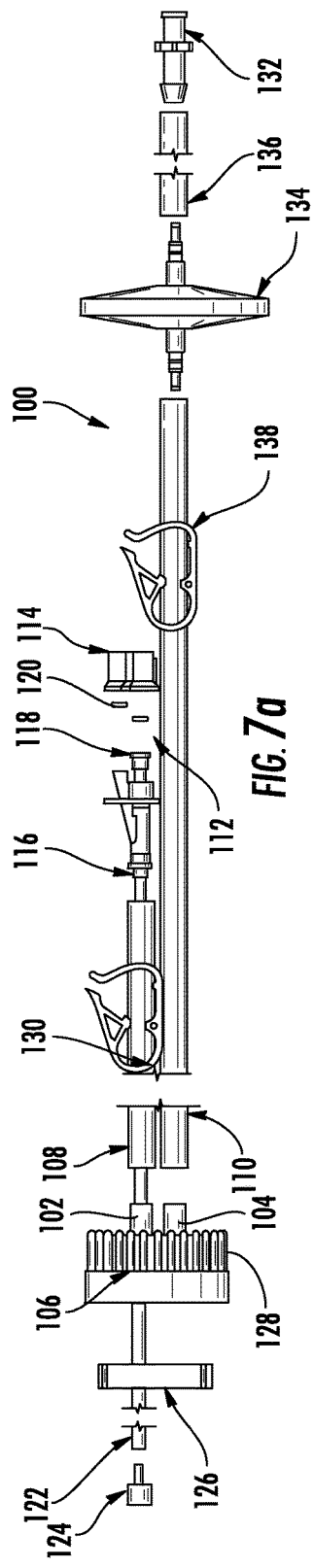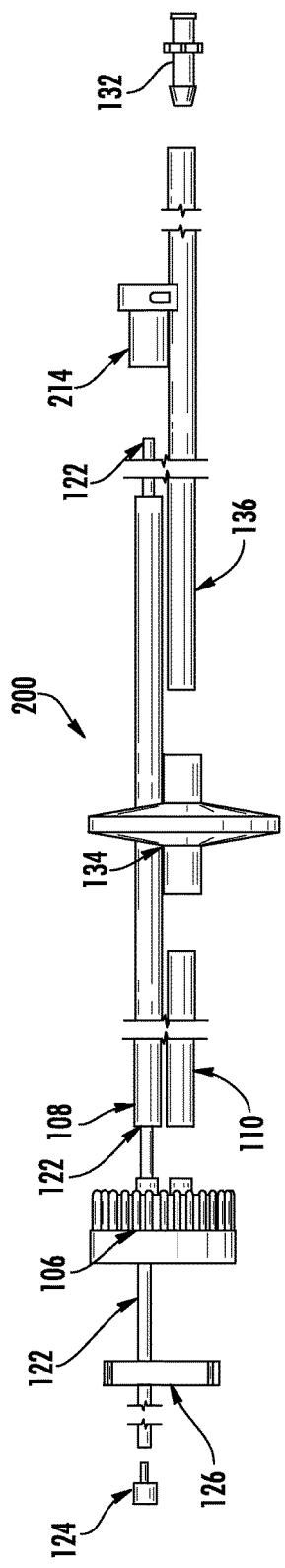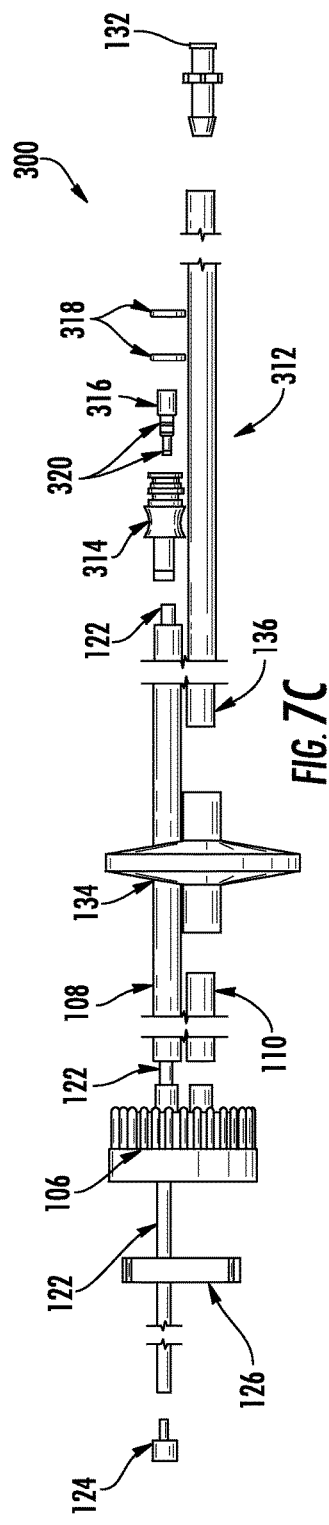

WATER BOTTLE CAP ASSEMBLIES FOR AN ENDOSCOPIC DEVICE

CROSS-REFERENCE TO RELATED APPLICATIONS

This application is a national stage application filed under 35 U.S.C. 371 of International Application No. PCT/US2013/032005, entitled "Water Bottle Cap Assemblies for an Endoscopic Device," filed Mar. 15, 2013, which claims priority from U.S. Provisional Appl. Ser. No. 61/618,054, filed on Mar. 30, 2012, the contents of each of which are incorporated herein in their entirety.

FIELD OF THE INVENTION

The present application is directed to devices used in surgical procedures, such as endoscopic procedures, and more particularly to a water bottle cap assemblies that can be connected to a water bottle and an apparatus, such as an endoscopic device.

BACKGROUND

Many invasive medical procedures that previously required major surgery are now performed using endoscopic instruments. Such instruments can provide an internal view of particular body parts, organs, or passages without requiring invasive surgery. Generally, an endoscopic instrument may include one or more channels through which miniaturized, flexible instruments can be inserted and advanced. The endoscope typically includes an elongated flexible insertion tube equipped at one end with an eyepiece or other viewing means and at the other end with an optical lens. The insertion tube transmits images or image-producing signals from the illuminated operative site to the viewing means to provide the instrument operator with full vision of the actions being performed at the instrument's working end.

The insertion tube of an endoscope also provides a flow passage for the delivery of fluid (e.g., liquid or gas) for irrigation, insufflation or other purposes. In conventional practice, it is necessary to provide a flow of sterile water across the optic lens to prevent the buildup of materials (e.g., surgical debris and body fluids) on the optic lens. This flow of water operates, in a sense, like a windshield wiper/washer assembly.

In common designs, an endoscopic instrument typically has a control body which is connected by a light guide tube to a light guide connector, which includes a plurality of connectors that can suitably receive various fittings. For example, the light guide connector can include a connector orifice that receives a grounding lug, a suction port, an air inlet, and a water inlet. As such, the air and water are delivered through the light guide connector, through the light guide tube and into the control body. Alternatively, the control body can also include a water port so as to allow water to be directly provided to the control body. Suitable valves are provided on the control body so as to control the flow of water through the control body and over the optic lens of the instrument.

For example, FIG. 1 illustrates an endoscope system. The endoscope is shown to include a shaft (insertion tube) connected to a control body that includes a biopsy port, air-water and suction valves, and angulation controls. The control body is connected to an umbilical (light guide connecting tube) that further connects to an electrical pin unit, which is directly connected to a light source and is connected via a video connection lead (and plug) to a video processor. Each of the tubes extends from the control body to a main body for effecting various connections to the endoscopic device (e.g., air/water bottle connection suction, etc.). The image produced by the endoscope is transmitted via a fiber optic bundle, or electronically from a charge-coupled device (CCD) chip. FIG. 1 illustrates a video monitor and attached keyboard for viewing images and inputting commands. The main body includes a port for a water bottle connector that connects to a water bottle for providing water to the endoscope.

The somewhat complex internal anatomy of the endoscope is further illustrated in FIG. 2, which shows a detailed view of the endoscope from FIG. 1. As shown in FIG. 2, the shaft incorporates an instrumentation channel extending from the entry biopsy port to the tip of the instrument.

Unexpectedly, there is usually a great expense associated with the delivery of sterile water in an endoscopy system. As shown in FIG. 1, the known practice has been to use a water bottle with a cap having a tube. This tube typically has a fitting at the end distal to the bottle to allow for connection to the air/water bottle connector port seen in FIG. 2. This fitting is usually specific to the particular endoscope manufacturer, such as Olympus®, Fujinon®, or Pentax®.

Ambient air is often pumped into the system to charge the water bottle. It can be desirable, however, to provide a secondary gas source to the endoscope instead of ambient air, such as carbon dioxide ($CO_2$). Irrigation may also be desired during an endoscopic procedure. However, a separate connection, pump, and water source are conventionally required in order to effectuate irrigation through the endoscopic device.

Therefore, there is a need for a water bottle cap assembly that is easily manufactured and cost effective. There is also a need for a water bottle cap assembly that is configured for use with a variety of endoscopic instruments, procedures (e.g., lens cleaning, secondary gas, and/or irrigation), and water sources. Moreover, there is a need for a water bottle cap assembly that is disposable so as to minimize cross contamination.

SUMMARY OF THE INVENTION

Embodiments of the present invention provide water bottle cap assemblies for use in endoscopy procedures. The inventive water bottle cap assemblies can be designed and shaped to function with endoscopic devices generally or may be designed and shaped to function with endoscopic devices having a particular structure unique to a single manufacturer of endoscopic devices. Similarly, the water bottle cap assemblies may be configured for use with a variety of different water sources. In light of their economical nature (and option for disposable, single or daily use), the inventive water bottle cap assemblies allow for provision of a secondary gas in an endoscopy. In one embodiment, the water bottle cap is configured to also support irrigation. These and other benefits of the present invention are more fully described herein.

In certain embodiments, the present invention provides water bottle cap assemblies that can be used with endoscopic devices. In particular, the water bottle cap assemblies allow for in-line placement between the endoscopic device and a water source. For example, the water bottle cap assembly may include a cap comprising a plurality of ports (e.g., two, three, four, etc.) and an engageable member (e.g., internal threads) configured to sealingly engage with a water source (e.g., a water bottle or suitable container for holding one or more fluids). The assembly also includes a plurality of tubular members, each tubular member coupled to a respective port so as to be in fluid communication therewith. The tubular members may be single or dual lumen for conveying fluid between the water source and the endoscopic device. In addition, the assembly includes an adaptor coupled to an end of one of the tubular members that is configured to engage with an endoscopic device. At least one of the tubular members may be configured to convey at least one fluid (e.g., water, air, or secondary gas) between the water source and the endoscopic device.

BRIEF DESCRIPTION OF THE DRAWINGS

Figure 1:
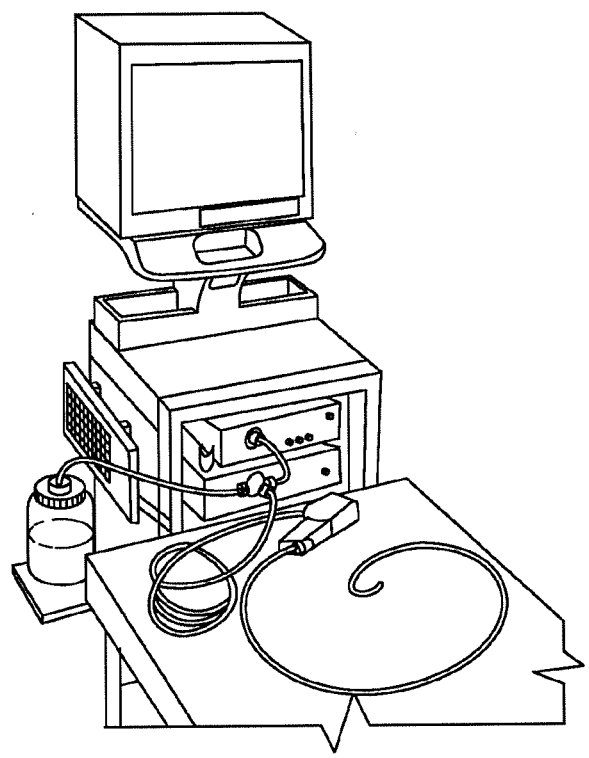
Figure 2:
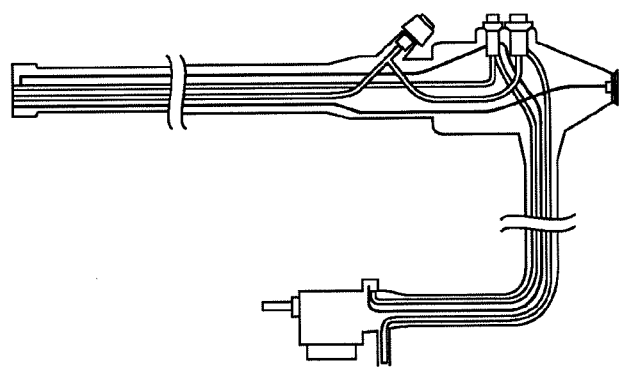
Figure 3:
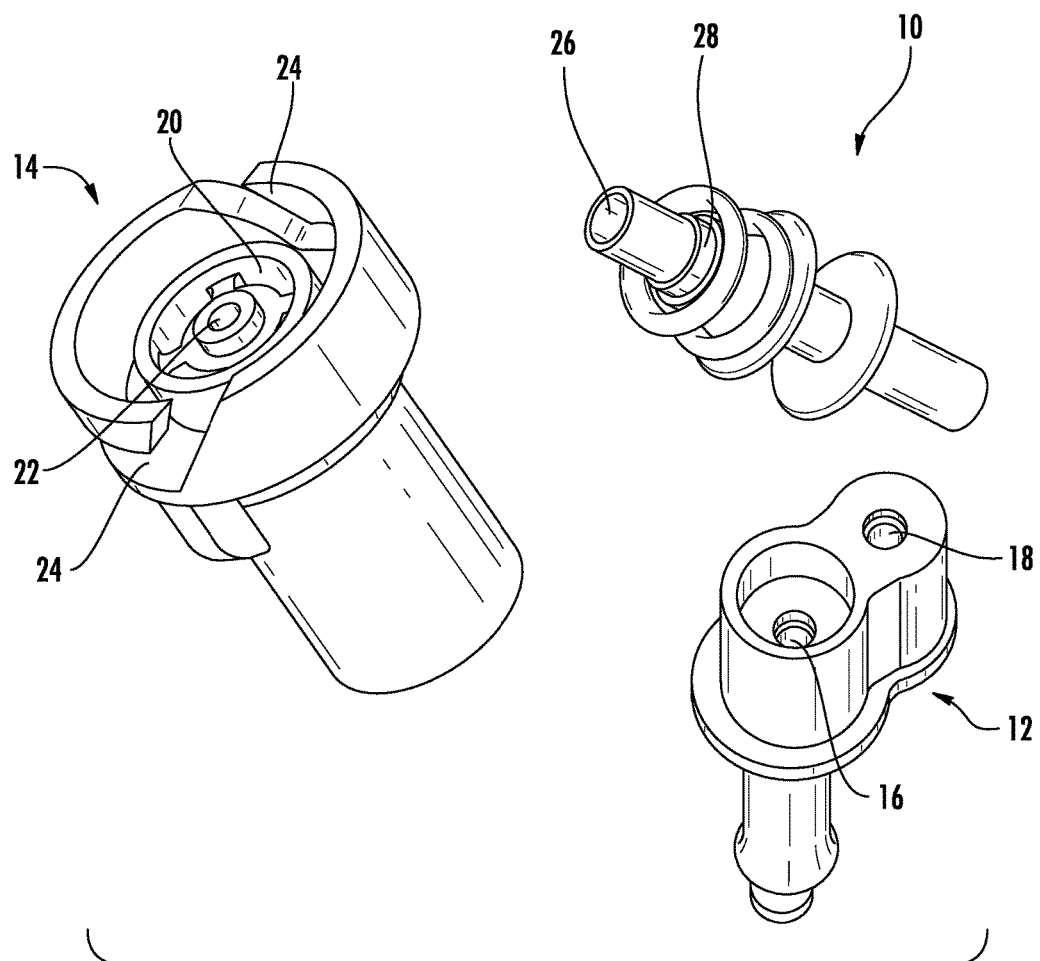
Figure 4A:
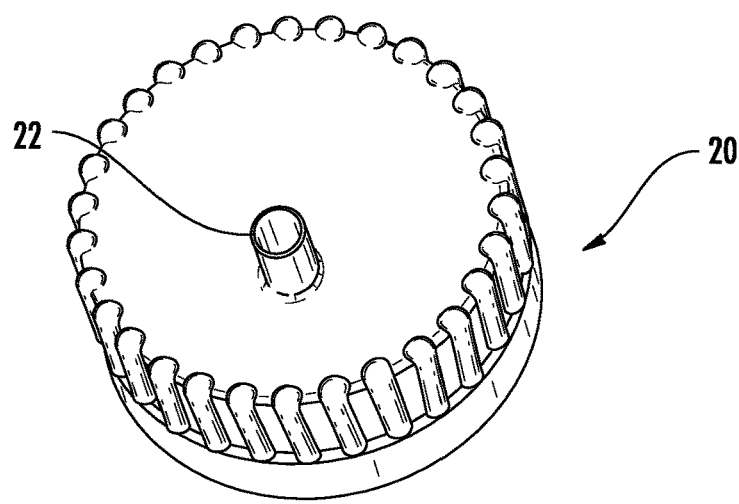
Figure 4B:
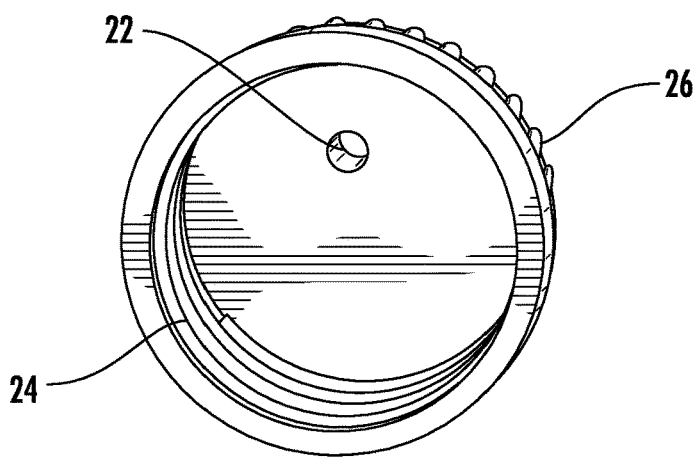
Figure 4C:
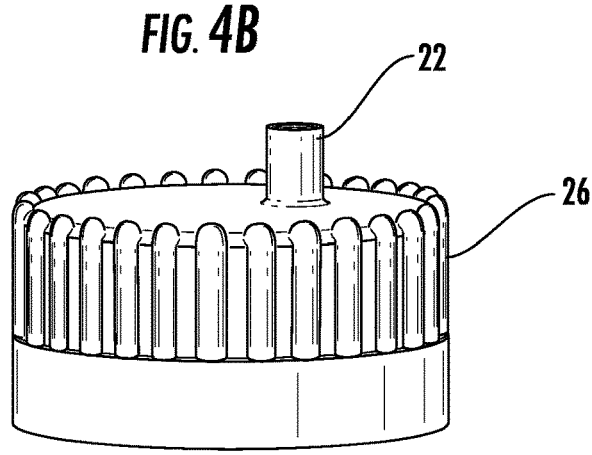
Figure 5A:
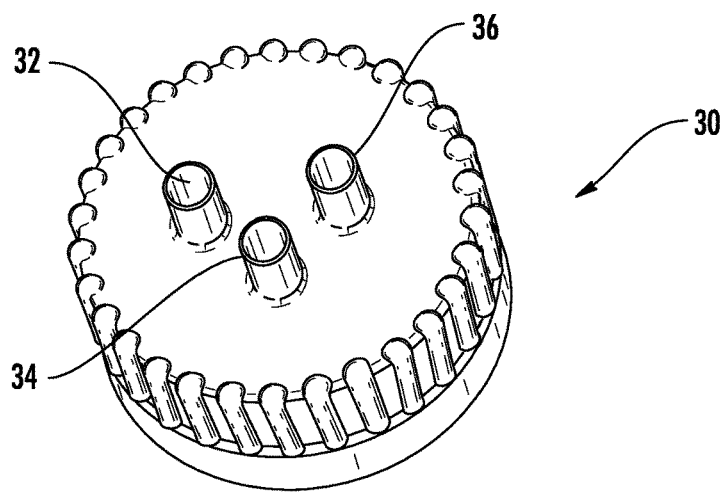
Figure 5B:
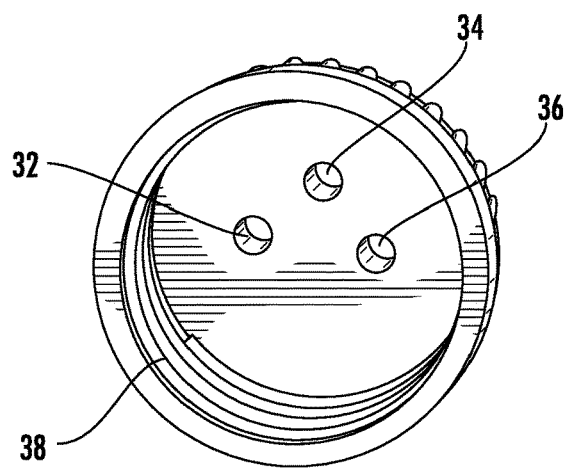
Figure 5C:
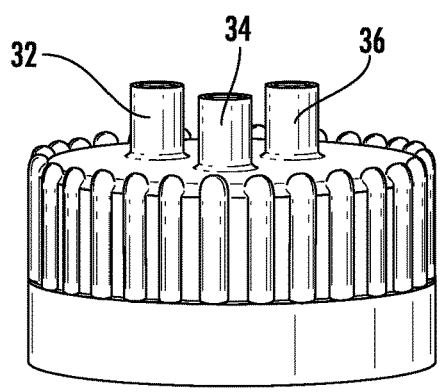
Figure 6A:
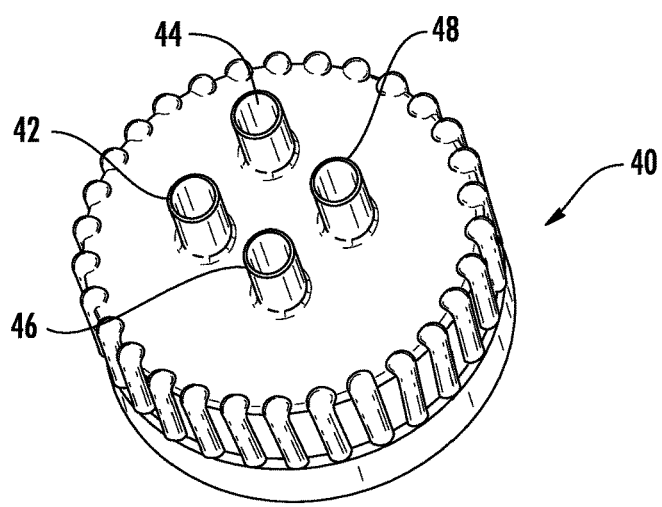
Figure 6B:
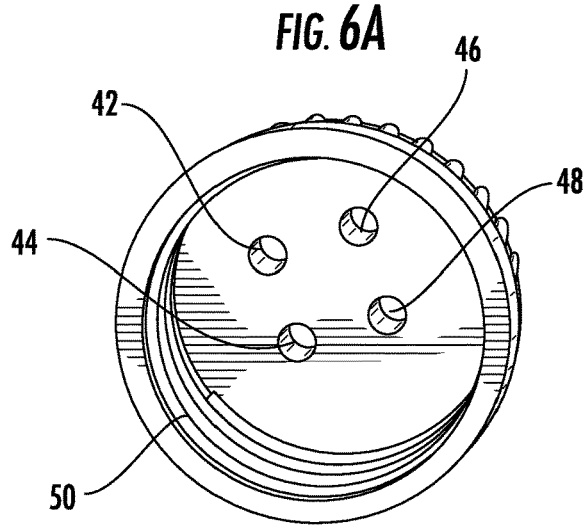
Figure 6C:
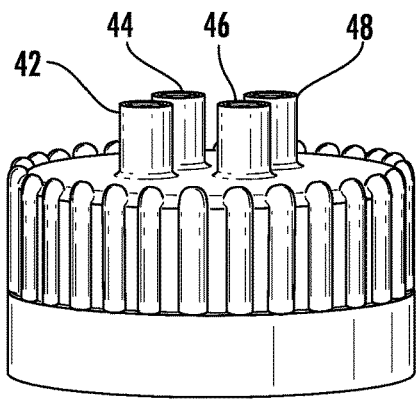
Figure 8:
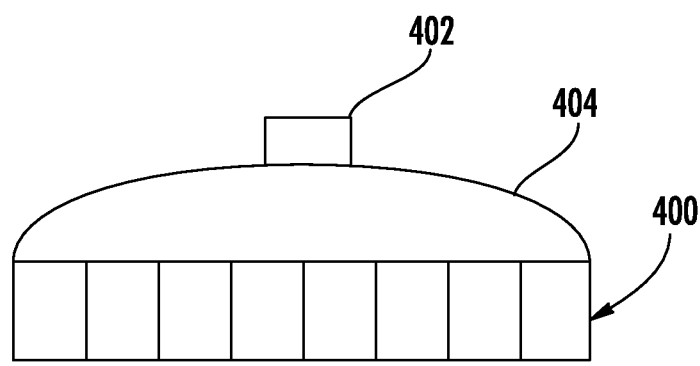
Figure 9:
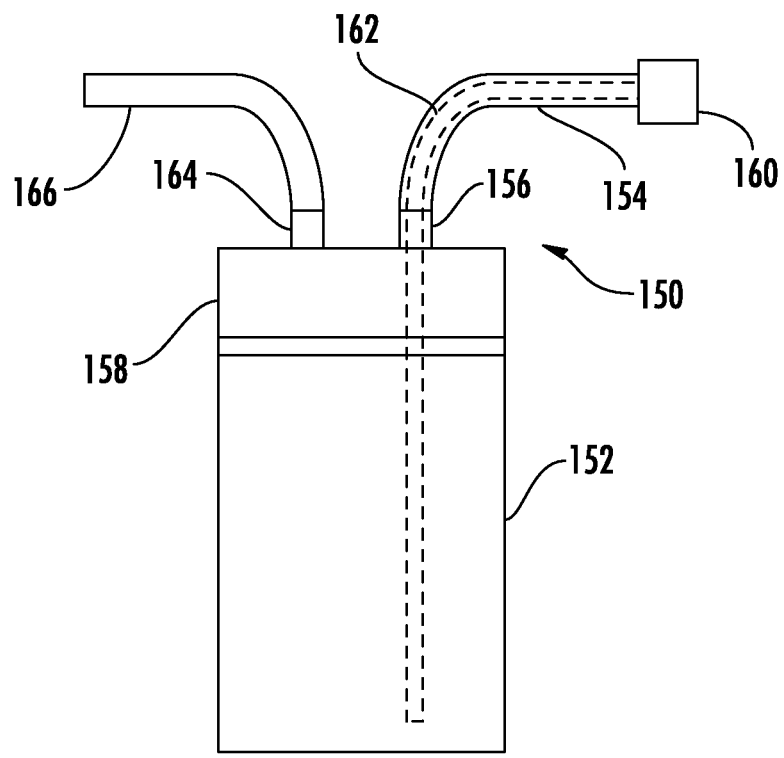

Having thus described the invention in general terms, reference will now be made to the accompanying drawings, which are not necessarily drawn to scale, and wherein:

FIG. 1 is an illustration of a conventional endoscope system;

FIG. 2 is a detailed view of the endoscope from the system illustrated in FIG. 1;

FIG. 3 is a perspective view of various adaptors configured to connect to a respective endoscopic device according to embodiments of the invention;

FIGS. 4A-4C are perspective views of a single-port water bottle cap according to one embodiment of the invention;

FIGS. 5A-5C are perspective views of a three-port water bottle cap according to one embodiment of the invention;

FIGS. 6A-6C are perspective views of a four-port water bottle cap according to one embodiment of the invention;

FIGS. 7A-7C are exploded views of water bottle cap assemblies according to embodiments of the invention;

FIG. 8 illustrates a side view of a water bottle cap according to another embodiment of the present invention; and FIG. 9 illustrates a water bottle cap assembled with a water bottle according to one embodiment of the present invention.

DETAILED DESCRIPTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Embodiments of the present invention are directed to water bottle cap assemblies configured for attachment between a water source and an endoscopic device during an endoscopic procedure. Endoscopic assemblies typically include a water source, such as a water bottle. In general, the water bottle cap assembly includes a cap configured to engage a water source and a tubing assembly having an adaptor configured to engage an endoscopic device. The cap may accommodate various needs for performing the endoscopic procedure using a single water source (e.g., providing water for instrument cleaning, air, a secondary gas source, and/or irrigation), while the adaptor may be varied for different types of endoscopic devices (e.g., Olympus®, Fujinon®, or Pentax® devices). Embodiments of the present invention may also be advantageous for use with a variety of disposable water bottles.

Introduction of a gas into a body cavity is common practice in gastrointestinal endoscopic procedures. Previously, when it has been desired to introduce a gas during an endoscopic procedure, standard room air was simply introduced (such as from the light source). More recently it has been found that the use of carbon dioxide ($CO_2$) insufflation can improve post-procedure patient comfort since $CO_2$ is more easily absorbed by the body. For example, use of $CO_2$ may be particularly useful for long endoscopic exams, such as endoscopic retrograde cholangiopancreatogram (ERCP), enteroscopy, and colonoscopy, and gas may be used in other endoscopic procedures as well, such as endoscopic ultrasound (EUS) and esophagogastroduodenoscopy (EGD). Provision of a secondary gas source has proven challenging, however. For example, the addition of $CO_2$ in an endoscopic procedure has previously required the use of cumbersome external regulators, flow meters, and specialized valves. The advent of specialized equipment for the provision of a secondary gas in an endoscopic procedure, such as the CO2EFFICIENT™ Endoscopic Insufflator (available from Bracco Diagnostics, Inc., Monroe Township, N.J.), has simplified secondary gas supply.

Different endoscopic devices are typically made by different manufacturers, thereby requiring a specific adaptor for coupling to the main body of the endoscopic device. For example, Pentax has available a gas adaptor that is designed exclusively for its endoscopic devices. Similarly Olympus and Fujinon each have specifically configured adaptors for attaching to respective endoscopic devices. According to embodiments of the present invention, each water bottle cap assembly includes an adaptor suitable for connection to a specific endoscopic device. For example, FIG. 3 illustrates a Pentax® adaptor 10, an Olympus® adaptor 12, and a Fujinon® adaptor 14. Of course, the water bottle cap assembly may be provided with other adaptor configurations depending on the endoscopic device employed. Thus, the connection of the adaptor to the endoscope main body can be facilitated in relation to the brand of endoscope. As noted previously, the three main manufacturers of endoscope devices make devices with significantly different structures. For example, a Pentax endoscope main body includes a connector with one or two pins extending from the outer surface of the connector. The Pentax® adaptor thus includes a slit for receiving the pin in rotational engagement. Alternatively, the adaptor may facilitate a press fit with the main body of the endoscopic device, such as is the case of the Pentax® and Olympus® adaptors.

Embodiments of the present invention are particularly beneficial in that the water bottle cap assemblies can be used with a wide variety of single-use, daily-use, or reusable water bottles. Generally, water bottles for use in endoscopy are of a somewhat standard size in relation to bottle volume, bottle neck diameter, and threads present. Thus, the water bottle cap assemblies of the invention can be made sized and configured to accommodate standard bottle neck sizes and threads. Thus, embodiments of the invention encompass a number of different embodiments of the water bottle cap assemblies that may vary only in the sizing of certain components of the water bottle assemblies.

FIGS. 4A-4C illustrate a water bottle cap 20 according to one embodiment of the present invention. The water bottle cap 20 includes a single port 22 extending outwardly from the cap. As shown, the port 22 protrudes outwardly from the exterior surface of the cap. The port 22 extends a sufficient length so as to be configured to engage a tubular member for providing a fluid to an endoscopic device (e.g., in a force fit). In one embodiment, the port 22 is configured to engage a dual-lumen tubular member that conveys air through one lumen to charge the water bottle and water through the other tube and to the endoscopic device. However, it is understood that the tubular member may have a single lumen if desired. The tubular member is configured to convey fluids between the water source and the endoscopic device (e.g., water and air). As used herein, the term "fluid" is intended to encompass any material that may be described in relation to flow, such as a gas or a liquid, including solutions or other physical forms of a liquid or a gas that may include some concentration of a solid material in a dissolved, suspended, or otherwise mixed state that does not prevent flow of the liquid or gas.

Moreover, FIG. 4B illustrates that the cap 20 includes interior threads 24 for engaging a water source, such as a water bottle. In one embodiment, the threads 24 on the interior surface of the cap 20 are suitable for attachment to the external threads on a water bottle. However, it is contemplated that the threads could be reversed if desired (i.e., external threads on the cap and internal threads in the water bottle). In this sense, the word "attach", when used in relation to a threaded attachment, is intended to mean a releasable arrangement wherein the various components can be attached or coupled together by a screwing motion utilizing the threads and also may be detached by unscrewing. In one embodiment, an outer surface of the cap 20 may include a gripping surface 26, such as raised ribs or a knurled surface, for facilitating rotation of the cap by a user.

FIGS. 5A-5C depict another embodiment of a water bottle cap 30 including three ports 32, 34, 36. Each of the ports is configured to engage a respective tubular member, wherein each tubular member has a single or multiple lumens. In the embodiment shown in FIGS. 5A-5C, one of the ports may be configured to couple to a dual-lumen tubular member for conveying fluids such as air for charging the water source to thereby deliver air and/or water to the endoscopic device. Another port may be configured to convey a secondary gas source (e.g., CO2). In the event a dual-lumen tubular member is employed for one of the ports, irrigation may also be provided for interfacing with an auxiliary forward water jet pump and forward water jet endoscope. Thus, the water bottle cap may include ports for selectively providing water for instrument cleaning and irrigation from the same water bottle. As before, the cap 30 includes interior threads 38 for mating with exterior threads on a water bottle.

FIGS. 6A-6C illustrate another embodiment of a water bottle cap 40. The water bottle cap 40 includes four ports 42, 44, 46, and 48. As before, each port is configured to engage a respective tubular member, whether single or dual-lumen. In one embodiment, each port is configured to receive a single lumen tubular member. For example, the tubular members may convey different fluids, such as air for charging the water source, water for cleaning the endoscopic lens, a secondary gas (e.g., CO2), and water for irrigation. In the instance where a dual-lumen tubular member is employed for one of the ports, the fourth port may be used to refill the water bottle during or between uses to accommodate procedures that require more than the maximum volume held by currently sold water bottles. The fourth port can also be used as an access point for the insertion of additional solid or liquid substances before, during, or after the procedure. The cap 40 also includes interior threads 50 for engaging external threads on a water bottle.

Furthermore, the water bottle cap assemblies shown in FIGS. 7A-7C include water bottle caps having two ports. For example, FIG. 7A shows two ports 102, 104 extending outwardly from the cap 106. In one embodiment, one of the ports 102 is configured to receive a dual-lumen tubular member (i.e., an outer tube 108 and an inner tube 122), while the other port 104 is configured to receive a single lumen tubular member 110. The outer tube 108 is coupled to the port 102 in a fluid-tight manner, such as using a force-fit connection. Similarly, the tubular member 110 is secured to the port 104 so as to be in fluid-tight communication. The inner tube 122 is disposed within the outer tube 108 so as to define a gap therebetween, wherein the gap is configured to convey a fluid between the water bottle and the endoscopic instrument. As such, the dual-lumen port 102 is configured to receive air between the inner tube 122 and the outer tube 108 for charging the water within the bottle for providing water through the inner tube 122 to the endoscopic instrument, while the second port 104 is configured to provide a secondary gas through the tubular member 110 to the endoscopic device. Thus, air can be provided into the water bottle to pressurize the water to convey air and/or water to the endoscopic device. The inner and/or outer tubes may be made of a variety of materials, including those that are water and CO2 resistant.

FIG. 7A illustrates that the water bottle cap assembly 100 includes an adaptor assembly 112. The adaptor assembly 112 includes an adaptor 114 suitable for connection with an endoscope main body, such as that manufactured by Olympus, in a press fit. FIG. 3 shows the adaptor assembly 12 in more detail wherein a pair of openings 16, 18 are defined therethrough. The opening 16 is configured to convey water therethrough via the inner tube 122, while the opening 18 is configured to convey air therethrough via the outer tube 108. In this regard, the inner tube 122 is typically configured to receive water therethrough, while the outer tube 108 is configured to receive air therethrough. The adaptor assembly further includes a Y-adaptor 116, a peg 118, and sealing members 120 (e.g., O-rings). The peg 118 is coupled to an end of the inner tube 122 that extends through the dual-lumen port 102 and into the water bottle. The peg 118 is configured to be inserted into the Y-adaptor 116 in a force or interference fit, while the adaptor 114 is secured to the Y-adaptor so as to compress the sealing members 120 therebetween. The assembly is secured together, such as via ultrasonic welding, although other suitable securing techniques may be used.

At the opposite end of the inner tube 122 is secured a weighted tip 124, wherein the weighted tip is configured to be positioned within the water bottle. The weighted tip 124 ensures that the inner tube is positioned at or near the bottom of the water bottle in order to sufficiently utilize the volume of fluid in the water bottle. The tip 124 may also include a channel or other structure defined on its end to prevent the tip from adhering to the bottom of the water bottle due to a suction force. An additional sealing member 126, such as a gasket, in the shape of a ring may be positioned within the cap 106 for ensuring a water tight connection between the cap and the water bottle when secured together. In addition, the sealing member 126 may be formed of a resilient material (e.g., a thermoplastic elastomer) such that the sealing member is configured to facilitate connection of the cap 106 to water bottles having different sizes and threads. In particular, the sealing member 126 may be configured to absorb any slack between the threads of the cap 106 and the water bottle threads while still maintaining a hermetic seal. Moreover, an outer surface of the cap 106 may include a gripping surface 128, such as raised ribs, for facilitating rotation of the cap by a user. A clip 130 may also be provided on the outer tube 108 that is configured to close off fluid communication between the water bottle and the endoscopic device, such as at the end of a procedure.

As discussed above, the single lumen tubular member 110 is coupled to the second port 104 so as to be in fluid communication therewith. A filter 134 may disposed on the end of the tubular member 110 for preventing ingress of viruses, microbes, and other harmful foreign substances from entering the water bottle. For example, the filter may have pores of about 0.2 micron, 0.1 micron, or less. The filter 134 may also serve to prevent backflow of liquid into the gas supply unit. In some cases, the filter may be a hydrophobic filter. In some embodiments, the filter 134 may be disposed as close as possible to the water source, such as within 12 inches of the water bottle. Where a filter 134 is employed, a tubing 136 is disposed between the filter and a coupling member 132 that is configured to couple to a gas supply unit. For example, the coupling member 132 may be a luer lock or of other suitable construction (e.g., barb, press fit, threads, etc.) for allowing connection and disconnection from a gas supply device. Similar to clip 130, the tubular member 110 may also include a clip 138 that is configured to close off fluid communication between the water bottle and the gas supply device, such as at the end of a procedure.

FIG. 7B illustrates another embodiment of a water bottle cap assembly 200. The water bottle cap assembly 200 is similar to that of FIG. 7A, but includes a different adaptor 214. In this regard, the adaptor 214 is suitable for connection to the main body of a Fujinon® endoscopic device. The adaptor 214 may be integrally formed and monolithic in construction. FIG. 3 shows the adaptor 14 in further detail whereby a plurality of openings 20 in fluid communication with the outer tube 108 surround a single opening 22 in fluid communication with the inner tube 122. The adaptor 14 is configured for a twist-fit connection with the main body whereby a pair of slots 24 engage a pair of pins on the main body of the endoscopic device.

FIG. 7C illustrates another embodiment of a water bottle cap assembly 300. The water bottle cap assembly 300 is similar to that of FIGS. 7A and 7B, but includes a different adaptor assembly 312. In this regard, the adaptor assembly 312 is suitable for connection to the main body of a Pentax® endoscopic device. The adaptor assembly 312 may be configured to connect to the main body in a press-fit. In general, the adaptor assembly 312 includes an adaptor 314, an insert 316, and a pair of sealing members 318 (e.g., O-rings). The insert 316 is partially inserted within an opening of the adaptor 314 until the insert is seated on a shelf and is secured in place. The opposite end of the adaptor 314 is coupled to the inner tube 122, while the sealing members 316 are placed into wells or grooves 320 defined on the outer surface of the adaptor. FIG. 3 shows an assembled view of the adaptor assembly, wherein an opening 26 defined through the insert 316 is configured to convey water therethrough via the inner tube 122, while one or more openings 28 defined between the insert and the adaptor are configured to convey air therethrough via the outer tube 108.

FIG. 9 illustrates a simplified depiction of a water bottle cap assembly 150 engaged with a water bottle 152. As shown, an outer tube 154 is engaged with a port 156 on the cap 158. An opposite end of the outer tube 154 is engaged with an adaptor 160 for engaging a main body of an endoscopic device. An inner tube 162 extends from the adaptor 160 and into the water bottle 152. A second port 164 on the cap 158 is configured to couple to a tubular member 166, such as for providing a secondary gas source.

It is understood that the aforementioned discussion is not meant to be limiting, as the construction of the water bottle assemblies 100, 200, 300 may be modified in further embodiments. For example, the tip 124 may be eliminated where a stiffer inner tube 122 is utilized, which would improve the assembly process while also ensuring use of the entire volume of water within the water bottle. In addition, although the cap has been shown as having a planar surface, the cap 400 may include a curved or domed surface 404 as shown, for example, in FIG. 8. A domed surface 404 may provide for a greater volume of air between the maximum water level height within the water bottle and the inner surface of the cap. This may prevent the currently practiced requirement of dumping out up to 33% of the volume of the water bottle to facilitate space required to reach necessary pressure levels inside of the water bottle. This feature may also allow for additional ports as more port space would be available on the cap as the surface area of the cap is increased. In addition, the water bottle cap assembly may include a check valve within the tubing (e.g., one valve per port) that could be placed within a tubular member on either side of the cap which would prevent the possibility of backflow and therefore further eliminate any chance of cross-contamination as the water bottle is used during its product lifespan. Furthermore, it is understood that the water bottle cap assemblies may include any number of adaptors for various manufacturers of endoscopic devices.

As discussed above, the water bottle cap may have one or more ports. In one embodiment, the cap may be created with all ports initially sealed off with removable sealing members and then only those ports used during a procedure would be opened. Thus, the sealing member would inhibit fluid flow through the ports. For example, the ports could be sealed off using a cap, pealable/pierceable material, or the like. This port selectability would allow for the production of a single cap configuration but allow for the assembly of multiple different products all utilizing the same cap. As such, the customer would be provided more flexibility in use of the water bottle cap, while also allowing for savings to the manufacturer in that different types of caps would be unnecessary.

The water bottle cap assemblies of the invention can be made of a variety of different materials, which may affect how the water bottle cap assemblies are formed. In general, the water bottle cap assemblies are formed of a sterilizable material (e.g., gamma sterilization). In certain embodiments, the components of the water bottle cap assemblies may be formed individually. As such, the water bottle cap assemblies particularly may comprise a plurality of individual parts that are formed separately and then combined to form the final water bottle cap assembly. Biocompatible bonding agents may also be utilized for joining components together (e.g., ultraviolet cure gamma sterilizable adhesive). Such combination can be by any means recognized as useful in the art, such as gluing, ultrasonic welding, or the like or using further attachment components, such as rivets, fasteners, or the like. It is understood that one or more components of the water bottle cap assemblies may be integrally formed. This particularly is advantageous for providing a combination of components as a single, monolithic structure, which provides for a seamless construction.

The water bottle cap assemblies of the invention are also beneficial in that they can be provided as a single-use or daily-use (e.g., disposable). For example, the water bottle assemblies may be packaged in sterile packaging and designed to be used once within a 24-hour time period after being opened. This is useful in instances where the water bottle is also disposable. In some embodiments, the inventive adaptor can be both disposable (e.g., single-use or daily-use) and reusable in that the end-user will have the option to dispose of the adaptor after a single use or at the end of the day, or to sterilize the adaptor and reuse it. This is achievable in particular because of the ability to form the water bottle cap assemblies from a variety of materials using a variety of methods. Thus, the water bottle cap assemblies can be sufficiently economical to justify making only a single use to avoid the need to sterilize. At the same time, the water bottle cap assemblies can be sufficiently sturdy to withstand multiple sterilization procedures.

The water bottle cap assemblies can be formed from a variety of different materials. In some embodiments, the water bottle cap assemblies comprise a polymeric material, which preferably is chemical resistant and/or heat resistant. The use of medical grade plastic materials is particularly desirable. Non-limiting examples of polymeric materials that may be used to form one or more component of the inventive adaptor include polyethylene (e.g., UHME-PE), polypropylene, polymethylmethacrylate (PMMA), acetal copolymers, polythermide, polycarbonate, polyvinylchloride, polysulfone (e.g., polyphenylsulfone), and polyetheretherketone (PEEK). The sealing members can be formed of any material recognized as useful in forming such elements, such as thermoplastic or natural or synthetic rubbers. It is also understood that the water bottle cap assemblies may be formed of one or more metal materials or combination of polymeric and metal materials.

Thus, embodiments of the present invention may provide several advantages. For example, the water bottle cap assemblies may be disposable and sterilizable. By providing a sterile and disposable water bottle cap assembly, cross-contamination risk is minimized and the risk associated with reprocessing errors is eliminated. Costs are thereby reduced, as reprocessing of endoscope-related accessories and components is a costly and labor intensive recurring problem that often requires a significant amount of premium floor space and capital investment. In addition, water bottle cap assemblies may support either CO2 or air insufflation without the need for a water bottle dedicated to one or the other. Thus, the functionality of the interface between the tubing and the endoscopic device is derived from the cap and not from the water bottle. Therefore, the water bottle cap assemblies are configured for use with a variety of different endoscopic procedures and with different types and sizes of water bottles.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A water bottle cap assembly for use with an endoscopic device, the assembly comprising:
   a cap comprising a dome-shaped outer surface and an engageable member, wherein the engageable member is configured to sealingly engage with a water source, and wherein the dome-shaped outer surface defines a plurality of ports to allow for a plurality of output configurations that allow assembly of multiple different products all utilizing the same cap, wherein each of the plurality of ports are initially sealed via a removable sealing member to initially prevent fluid from flowing therethrough,
   a plurality of tubular members, wherein each tubular member is coupled to a respective port so as to be in fluid communication therewith, wherein at least one of the tubular members being a single lumen tubular member comprising a coupling member for coupling to a gas supply unit;
   an adaptor coupled to an end of one of the tubular members and configured to engage with an endoscopic device, at least one of the tubular members configured to convey at least one fluid between the water source and the endoscopic device; and
   a filter disposed on the single lumen member and within 12 inches of the water source to filter contaminants from entering the water source and to prevent backflow to the gas supply unit, wherein the filter comprises pores of about 0.1 micron.

2. The water bottle cap assembly of claim 1, wherein the engageable member comprises internal threads.

3. The water bottle cap assembly of claim 1, further comprising a ring-shaped sealing member disposed within the cap and configured to facilitate engagement with the water source.

4. The water bottle cap assembly of claim 1, wherein the cap is configured to accommodate a volume of air between a maximum water level height and an interior of the dome-shaped outer surface of the cap.

5. The water bottle cap assembly of claim 1, further comprising a check valve disposed within at least one of the tubular members and configured to prevent fluid flow into the water source.

6. The water bottle cap assembly of claim 1, wherein the cap comprises two, three, or four ports.

7. The water bottle cap assembly of claim 1, wherein at least one of the tubular members comprises a dual-lumen tubular member such that an inner tube extends within an outer tube.

8. The water bottle cap assembly of claim 1, wherein at least one of the tubular members is configured to convey a gas source between the water source and the endoscopic device.

9. The water bottle cap assembly of claim 1, wherein at least one of the tubular members is configured to convey water between the water source and the endoscopic device for irrigation.

10. The water bottle cap assembly of claim 1, wherein the water bottle cap assembly is formed of a sterilizable polymeric material and is disposable.

11. The water bottle cap assembly of claim 1, wherein the filter is a hydrophobic filter.

12. A water bottle cap assembly for use with an endoscopic device, the assembly comprising:
   a cap comprising an engageable member configured to sealingly engage with a water source, wherein the cap defines four ports, the four ports opening into a fluid storage chamber defined by the water source and the cap,
   the fluid storage chamber configured to accommodate a volume of air between a maximum water level height of the water source and an interior of the cap, wherein each of the four ports is initially sealed off with a removable sealing member to prevent fluid through the associated port, and wherein each of the removable sealing members comprise at least one of a peelable material and a pierceable material, a plurality of tubular members, each tubular member coupled to a respective port so as to be in fluid communication therewith, at least one of the tubular members being a single lumen tubular member comprising a coupling member configured to couple to a gas supply unit;

an adaptor coupled to an end of one of the tubular members and configured to engage with an endoscopic device, at least one of the tubular members configured to convey at least one fluid between the water source and the endoscopic device; and a filter disposed on the single lumen member and within 12 inches of the water source to filter contaminants from entering the water source and to prevent backflow to the gas supply unit, wherein the filter comprises pores of about 0.1 micron, wherein the volume of air allows a pressure level of the water source to be increased to a level sufficient for conveying the at least one fluid from the water source through at least one of the tubular members.

13. The water bottle cap assembly of claim 12, wherein the cap comprises a dome-shaped outer surface.

14. The water bottle cap assembly of claim 12, wherein at least one of the tubular members is configured to convey water between the water source and the endoscopic device for irrigation.

15. The water bottle cap assembly of claim 12, wherein the filter is a hydrophobic filter.

* * * * *